(12) United States Patent
Mishra

(10) Patent No.: US 8,444,969 B2
(45) Date of Patent: May 21, 2013

(54) NEUTROPHIL-DEPLETED PLATELET RICH PLASMA FORMULATIONS FOR CARDIAC TREATMENTS

(76) Inventor: Allan Mishra, Menlo Park, CA (US)

(*) Notice: Subject to any disclaimer, the term of this patent is extended or adjusted under 35 U.S.C. 154(b) by 0 days.

(21) Appl. No.: 13/333,082

(22) Filed: Dec. 21, 2011

(65) Prior Publication Data

US 2012/0093941 A1 Apr. 19, 2012

Related U.S. Application Data

(63) Continuation of application No. 12/576,101, filed on Oct. 8, 2009.

(60) Provisional application No. 61/104,074, filed on Oct. 9, 2008.

(51) Int. Cl.
*C12N 5/078* (2010.01)

(52) U.S. Cl.
USPC ............... 424/93.72; 424/93.71; 435/372

(58) Field of Classification Search
None
See application file for complete search history.

(56) References Cited

U.S. PATENT DOCUMENTS

| | | | |
|---|---|---|---|
| 4,414,108 A | 11/1983 | Ito | |
| 4,957,742 A | 9/1990 | Knighton | |
| 5,147,776 A | 9/1992 | Koerner, Jr. | |
| 5,165,938 A | 11/1992 | Knighton | |
| 5,178,883 A | 1/1993 | Knighton | |
| 5,403,272 A | 4/1995 | Deniega et al. | |
| 5,474,891 A | 12/1995 | Murphy | |
| 5,494,590 A | 2/1996 | Smith et al. | |
| 5,510,102 A | 4/1996 | Cochrum | |
| 5,578,460 A | 11/1996 | Ebersole et al. | |
| 5,578,565 A | 11/1996 | Chao et al. | |
| 5,585,007 A | 12/1996 | Antanavich et al. | |
| 5,599,558 A | 2/1997 | Gordinier et al. | |
| 5,614,204 A | 3/1997 | Cochrum | |
| 5,643,786 A | 7/1997 | Cohen et al. | |
| 5,676,849 A | 10/1997 | Sammons et al. | |
| 5,733,545 A * | 3/1998 | Hood, III ................... | 424/93.72 |
| 5,773,033 A | 6/1998 | Cochrum et al. | |
| 5,785,869 A | 7/1998 | Martinson et al. | |
| 5,788,662 A | 8/1998 | Antanavich et al. | |
| 5,834,418 A | 11/1998 | Brazeau et al. | |
| 5,916,743 A | 6/1999 | Lake et al. | |
| 5,928,214 A | 7/1999 | Rubinstein et al. | |
| 5,993,804 A | 11/1999 | Read et al. | |
| 6,063,297 A | 5/2000 | Antanavich et al. | |
| 6,098,631 A | 8/2000 | Holoshitz et al. | |
| 6,210,976 B1 | 4/2001 | Sabbadini | |
| 6,214,338 B1 | 4/2001 | Antanavich et al. | |
| 6,432,119 B1 | 8/2002 | Saadat | |
| 6,444,228 B1 | 9/2002 | Baugh et al. | |
| 6,596,179 B2 | 7/2003 | Giesler et al. | |
| 6,811,777 B2 | 11/2004 | Mishra | |
| 6,905,612 B2 | 6/2005 | Dorian et al. | |
| 6,942,639 B2 | 9/2005 | Baugh et al. | |
| 6,942,880 B1 | 9/2005 | Dolecek et al. | |
| 7,169,547 B2 | 1/2007 | Rubinstein et al. | |
| 7,211,191 B2 | 5/2007 | Coelho et al. | |
| 7,252,758 B2 | 8/2007 | Dolecek et al. | |
| 7,314,617 B2 | 1/2008 | Mishra | |
| 7,608,258 B2 | 10/2009 | Mishra | |
| 7,708,152 B2 | 5/2010 | Dorian et al. | |
| 2002/0004038 A1 | 1/2002 | Baugh et al. | |
| 2002/0058030 A1 | 5/2002 | Monroy et al. | |
| 2002/0147611 A1 | 10/2002 | Greene et al. | |
| 2003/0116512 A1 | 6/2003 | Antwiller et al. | |
| 2003/0152639 A1 | 8/2003 | Britton et al. | |
| 2003/0175248 A1 | 9/2003 | Uhr | |
| 2003/0191005 A1 | 10/2003 | Coelho et al. | |
| 2003/0205538 A1 | 11/2003 | Dorian et al. | |
| 2003/0233064 A1 | 12/2003 | Arm et al. | |
| 2003/0233065 A1 | 12/2003 | Steward et al. | |
| 2004/0091459 A1 * | 5/2004 | Nimni ........................... | 424/93.7 |
| 2004/0131583 A1 | 7/2004 | Barritault et al. | |
| 2004/0182795 A1 | 9/2004 | Dorian et al. | |
| 2005/0186193 A1 | 8/2005 | Mishra | |
| 2005/0209081 A1 | 9/2005 | Baugh et al. | |

(Continued)

FOREIGN PATENT DOCUMENTS

| | | |
|---|---|---|
| EP | 0 142-339 | 5/1985 |
| EP | 0 417 818 | 3/1991 |

(Continued)

OTHER PUBLICATIONS

Esa, et al. "Immunological Heterogeneity of Human Monocyte Subsets Prepared by Counterflow Centrifugation Elutriation," Immunology, vol. 59, pp. 95-99, 1986.

Sharpe, P.T., Chapter 5, Centrifugal Elutriation, R.H. Burdon and P.H. van Knippenberg editors, Laboratory Techniques in Biochemistry and Molecular Biology, Elsevier Science Publishers, Amsterdam, NL, pp. 91-94, 97-100, 101 and 105, 1998.

Rink, "Cytosolic Calcium in Platelet Activation," *Cellular and Molecular Life Sciences*, vol. 44, No. 2, pp. 97-100, downloaded from http://www.springerlink.com/content/j41h051h8866m352/?target=print, Abstract print, Feb. 1988.

Dohan Ehrenfest, et al. "Classification of Platelet Concentrates: from Pure Platelet-rich Plasma (P-PRP) to Leucocyte- and Platelet-rich Fibrin (L-PRF)," *Trends in Biotechnology*, vol. 27, No. 3, pp. 158-167, 2008.

(Continued)

*Primary Examiner* — L J Schuberg
(74) *Attorney, Agent, or Firm* — Knobbe, Martens, Olson & Bear LLP

(57) ABSTRACT

Compositions and methods for preparing neutrophil-depleted platelet rich plasma are provided. Generally, these compositions comprise a higher concentration of platelets and depressed concentrations of neutrophils relative to whole blood although white blood cells may be at higher concentrations than whole blood. The concentrations of the platelets and/or the white blood cells may be two to eight times the respective concentrations in whole blood. These compositions may have depressed concentrations of red blood cells and hemoglobin. In some variations, the compositions may be useful to treat damaged connective tissue and/or to slow or stop cardiac apoptosis after a heart attack. The neutrophil-depleted platelet rich plasma composition may be delivered in conjunction with reperfusion therapy.

17 Claims, 2 Drawing Sheets

U.S. PATENT DOCUMENTS

| | | |
|---|---|---|
| 2006/0041243 A1 | 2/2006 | Nayak et al. |
| 2006/0068369 A1 | 3/2006 | Coelho et al. |
| 2006/0127382 A1 | 6/2006 | Mishra |
| 2006/0263407 A1 | 11/2006 | Mishra |
| 2007/0014784 A1 | 1/2007 | Nayak et al. |
| 2007/0020735 A1 | 1/2007 | Chen et al. |
| 2007/0042016 A1 | 2/2007 | Nayak et al. |
| 2007/0172472 A1 | 7/2007 | Nayak |
| 2007/0179424 A1 | 8/2007 | Rubinstein et al. |
| 2007/0202093 A1 | 8/2007 | Brooks et al. |
| 2007/0269887 A1 | 11/2007 | Coelho et al. |
| 2008/0045964 A1 | 2/2008 | Mishra |
| 2008/0069777 A1 | 3/2008 | Cohen et al. |
| 2008/0081367 A1 | 4/2008 | Sowemimo-Coker et al. |
| 2008/0248081 A1 | 10/2008 | Mishra |
| 2008/0248082 A1 | 10/2008 | Mishra |
| 2008/0248083 A1 | 10/2008 | Mishra |
| 2008/0248084 A1 | 10/2008 | Mishra |
| 2008/0248085 A1 | 10/2008 | Mishra |
| 2008/0254093 A1 | 10/2008 | Mishra |
| 2008/0255471 A1 | 10/2008 | Naghavi et al. |
| 2009/0053208 A1 | 2/2009 | Nayak |
| 2009/0092679 A1 | 4/2009 | Mishra |
| 2009/0254104 A1 | 10/2009 | Murray |
| 2010/0092444 A1 | 4/2010 | Mishra |
| 2010/0112081 A1 | 5/2010 | Mishra |
| 2010/0140182 A1 | 6/2010 | Chapman et al. |
| 2010/0150892 A1 | 6/2010 | Han |
| 2010/0183561 A1 | 7/2010 | Sakthivel et al. |

FOREIGN PATENT DOCUMENTS

| | | |
|---|---|---|
| JP | 5-500516 | 2/1993 |
| WO | WO 91/04035 | 4/1991 |
| WO | WO 00/12018 | 3/2000 |
| WO | WO 00/54661 | 9/2000 |
| WO | WO 2011/127071 | 10/2011 |

OTHER PUBLICATIONS

International Search Report issued to related international applicaton PCT/US2009/60061 and dated Dec. 9, 2009.

Boldt et al. "Acute platelet-rich plasmapheresis for cardiac surgery" Journal of Cardiothoracic and Vascular Anesthesia, Saunders, Philadelphia, PA, U.S., vol. 9, No. 1, Feb. 1, 1995, pp. 79-88, XP005227129, ISSN: 1053-0770, LNKD-DOI:10.1016/S1053-0770(05)80061-8.

CD15 MicroBeads, Miltenyi Biotec Inc., downloaded from www.miltenyibiotec.com, pp. 4, 2008.

Cell Factor Technologies, Inc., Brochure for Boost Demineralizedbonematrix, 6 pages, 2004.

Cell Factor Technologies, Inc., Brochure for GPS II Platelet Concentrate System, 10 pages, 2004.

Chen, et al., PMA-activated Neutrophils Decrease Pulmonary Endothelial Ectoenzyme Activities in Perfused Rabbit Lungs, American Journal of Physiology, Dec. 1992, vol. 263, Issue 6, pp. L650-L656.

Colditz, et al., Neutrophil Accumulation and Plasma Leakage Induced in vivo by Neutrophil-Activating Peptide-1, Journal of Leukocyte Biology, 1990, vol. 48, pp. 129-137.

Cotler, et al., "The pH Dependence of Quantitative Ristocetin-Induced Platelet Aggregation: Theoretical and Practical Implications—A New Device for Maintenance of Platelet-Rich Plasma pH," *Blood*, vol. 47, No. 5, pp. 841-854, May 1976.

Cotter et al., "A Novel Method for Isolation of Neutrophils from Murine Blood Using Negative Immunomagnetic Separation," The American Journal of Pathology, vol. 159, pp. 473-481, 2001.

DePuy AcroMed, Inc. Brochure for Symphony Platelet Concentrate System, 10 pages, 2001.

Eppley et al. "Platelet Quantification and Growth Factor Analysis from Platelet-Rich Plasma: Implications for Wound Healing," Plastic and Reconstructive Surgery, pp. 1502-1508, vol. 114, No. 6, Nov. 2004.

Feuerstein, et al., "Congestive Heart Failure and Genomic Medicine: A Look into the 21$^{st}$ Century," *Cardiovascular Drugs and Therapy*, vol. 11, No. 6, 713-717, 1997.

Gawaz, et al. "Platelet Function in Acute Myocardial Infarction Treated with Direct Angioplasty," *Circulation*, vol. 93, pp. 229-237, 1996 with "Methods, Specimen Collection, Methods, Platelet Aggregation in Vitro, Discussion, Platelet Adhesion to Endothelium in AMI," downloaded from http://circ.ahajournals.org/cgi/content/full/93/2/229 on Dec. 2, 2009.

Gehring et al., "Preparation of autologous platelets for the opthalmologic treatment of macular holes", Transfusion 39: 144-148 (1999).

Giordano et al. "Autologous platelet-rich plasma in cardiac surgery: Effect on intraoperative and postoperative transfusion requirements" Journal of Cardiothoracic Anesthesia, Grune & Stratton, Orlando, FL, U.S., vol. 3, No. 3, Jun. 1, 1989, p. 376, XP026263096, ISSN: 0888-6296, LNKD-DOI:10.1016/0888-6296(89)90129-4.

Harvest Technologies GmbH Brochure for SmartPReP 2, 2002.

lba, et al., Angiogenesis by Implantation of Peripheral Blood Mononuclear Cells and Platelets into Ischemic Limbs, Circulation, 2002, vol. 106, pp. 2019-2025.

Knebel, et al., "Heart Failure: State of the Art Treatment and Options," *Clinical Nephrology*, vol. 60, Suppl. 1, pp. S59-S66, 2003.

Li et al., "Effects on Intramyocardial Injection of Platelet-rich Plasma on the Healing Process after Myocardial Infarction," Coronary Artery Disease, vol. 19, Issue 5, pp. 363-370, Aug. 2008.

Martinez-Gonzalez et al. "Do Ambulatory-Use Platelet-Rich Plasma (PRP) Concentrates Present Risks," Medicina Oral, vol. 7, pp. 375-390, 2002.

Ohman, et al. "Cardiac Troponin T Levels for Risk Stratification in Acute Myocardial lschemia," *The New England Journal of Medicine*, vol. 335, No. 18, pp. 1333-1341, Oct. 31, 1996.

Okuda, "Application of PRP (Platelet Rich Plasma) to Periodontal Treatment," Dental Outlook, vol. 98, No. 4, pp. 874-875, 2001 with English translation.

Palatianos, et al., Neutrophil Depletion Reduces Myocardial Reperfusion Morbidity, Annals of Thoracic Surgery, 2004, vol. 77, pp. 956-961.

Paques et al., "Effect of Autologous Platelet Concentrate in Surgery for Idiopathic Macular Hole", Ophthalmology 106 (5): 932-938 (1999).

Pruijt, et al., Neutrophils are Indispensable for Hematopoietic Stem Cell Mobilization Induced by Interleukin-8 in Mice, PNAS, Apr. 30, 2002, vol. 9, Issue 9, pp. 6228-6233.

Racz, et al., Buffy Coat or Platelet-rich Plasma?, Vox Sang, 1984, vol. 47, pp. 108-113.

Shim et al. "Stem Cell Cardiomyoplasty: State-of-the-Art," Annals of the Academy of Medicine, Singapore, vol. 33, No. 4, pp. 451-460, 2004.

Snyder, et al., "Calcium-Dependent Proteolysis of Actin During Storage of Platelet Concentrates," *Blood*, vol. 73, No. 5, pp. 1380-1385, 1989.

Tang, et al., "The Effects of pCO2 and pH on Platelet Shape Change and Aggregation for Human and Rabbit Platelet-Rich Plasma," *Thrombosis Research*, vol. 10, No. 1, pp. 135-146, 1977.

Valant, et al., Thrombotic Thrombocytopenic Purpura Plasma Enhances Platelet-Leukocyte Interaction in Vitro, British Journal of Haematology, 1998, vol. 100, pp. 24-32.

Valeri, Volume of RBCs, 24- and 48-hour posttransfusion survivals and lifespan of 51 Cr and biotin-X-N-hydroxysuccinimide (NHS)-labeled autologous baboon RBCs: effect of the anticoagulant and blood pH on 51 Cr and biotin-X-NHS elution in vivo, Transfusion, 2002, vol. 42, pp. 343-348.

Vassallo et al., "A Critical Comparison of Platelet Preparation Methods," Current Opinion in Hematology, vol. 13, pp. 323-330, 2006.

Yang et al., "Dielectric Properties of Human Leukocyte Subpopulations Determined by Electrorotation as a Cell Separation Criterion," Biophysical Journal, vol. 76, pp. 3307-3314, Jun. 1999.

* cited by examiner

| PRP Data (Murine) | | |
|---|---|---|
| WB = Whole Blood | | |
| PRP = Platelet Rich Plasma | | |
| | | |
| Type of Cell | Raw Value | Ratios |
| Platelets WB | 135 | |
| Platelets PRP | 628 | 4.65x |
| Red Cells WB | 4.46 | |
| Red Cell PRP | 1.2 | 0.26x |
| Hb WB | 13.8 | |
| Hb PRP | 3.5 | 0.25x |
| WBC WB | 4.5 | |
| WBC PRP | 19.9 | 4.42x |
| Neutrophils WB | 2790 cells/uL | |
| Neutrophils PRP | 12139 cells/uL | 4.35x |
| Lymphocytes WB | 1305 cells/uL | |
| Lymphocytes PRP | 6169 cells/uL | 4.73x |
| Monocytes WB | 270 cells/uL | |
| Monocytes PRP | 1194 cells/uL | 4.42x |
| Eosinophils WB | 270 cells/uL | |
| Eosinophils PRP | 398 cells/uL | 1.47x |
| Basophils WB | 0 cells/uL | |
| Basophils PRP | 0 cells/uL | 0x |

Figure 1

NEUTROPHIL-DEPLETED PLATELET RICH PLASMA FORMULATIONS FOR CARDIAC TREATMENTS

RELATED APPLICATIONS

This application is a continuation of U.S. application Ser. No. 12/576,101, filed Oct. 8, 2009 which claims priority to U.S. Provisional Application No. 61/104,074, filed Oct. 9, 2008. Both applications are incorporated herein by reference in their entirety.

FIELD OF THE INVENTION

The present application relates generally to formulations of a platelet rich plasma that may be used to treat various medical conditions. More specifically, the formulations of platelet rich plasma may comprise different levels of platelets and white blood cells relative to whole blood. In some variations, the formulations may comprise monocytes at a concentration that is at least two times a monocyte concentration in whole blood; lymphocytes at a concentration that is at least two times a lymphocyte concentration in whole blood; and eosinophils at a concentration that is about 1.5 times an eosinophil concentration in whole blood.

BACKGROUND

Tissue damage and degeneration may be both a cause and an effect of various medical conditions. Causes of damage may range from mechanical injury to other complex physiological processes involving inflammation and the like. For example, tissue damage may be the result of injury, overuse, reduced blood flow, or any other suitable cause. Even if the damage is halted or slowed, the tissue may not completely heal due to the formation of degenerative, immature, avascular, and scar tissue.

Connective tissues, such as tendons, ligaments, joint capsules, fascial tissues, and the like may be especially prone to damage. The overall prevalence of musculoskeletal disorders, for example, is approximately 140 per 1000 persons in the United States, according to a 1995 survey by the National Center for Health Statistics. The same survey estimated the direct costs to be $88.7 billion and the indirect costs estimated to be up to $111.9 billion for lost productivity. Musculoskeletal injures may be resistive to standard treatments such as anti-inflammatory medication, bracing, rest and physical therapy. Injuries or other damage to flexible, relatively avascular connective tissues (hereafter "connective tissue" or "connective tissues") may take a very long time to heal (e.g., months or even years). In many cases, injuries to connective tissues may never heal properly, and may require surgical intervention.

One example of a musculoskeletal disorder is lateral epicondylitis. Lateral epicondylitis or "tennis elbow" is a well-known sports medicine and orthopedic disorder that is often associated with to overuse injury and microtearing of the extensor carpi radialis brevis tendon at the elbow. The body attempts to repair these microtears but the healing process is incomplete in many cases. Pathologic specimens of patients undergoing surgery for chronic lateral epicondylitis reveal a disorganized angiofibroblastic dysplasia. This incomplete attempt at repair results in degenerative, immature, and avascular tissue. This incompletely repaired tissue may be weaker than normal tendon tissue and may lack normal function. This inadequate healing may continue to cause pain and may negatively impact the patient's ability to perform daily activities and the patient's quality of life.

Similar incomplete healing may be present in other types of musculoskeletal injuries or damage, such as patellar tendonitis (Jumper's Knee), Achilles tendonitis (common in runners), rotator cuff tendonitis (commonly seen in "overhead" athletes such as baseball pitchers), chronic injuries of the ankle ligaments ("ankle sprains"), or ligament tears.

Presently, many different non-operative and operative treatments exist. The non-operative measures include rest, activity modification, oral anti-inflammatory medication, and cortisone injections. While rest and activity modification may help patients with some of these conditions, there remains a significant clinical population that is not adequately treated with these therapies. Despite widespread use, oral anti-inflammatory medications have not proven to be useful in controlled studies. Some studies further suggest that non-steroidal medication may actually have an adverse effect on the healing process for ligament injuries. Also, no acute inflammatory cells have been found in pathologic samples of cases of lateral epicondylitis. Cortisone injections are controversial in the treatment of tendinoses and are contraindicated in acute ligament injuries. Several studies have noted an improvement in patients treated with cortisone in short term follow up, but longer term results beyond one year have revealed a high symptom recurrence rate and only an equivocal efficacy rate. These injections also carry the risk of tendon rupture, infection, skin depigmentation, subdermal atrophy, and hyperglycemia in diabetic patients. The operative measures include debridement and repair of the associated pathologic tendons. However, open or arthroscopic surgery has many potential complications such as deep infection, damage to neurovascular structures, and scar formation. The surgery is also expensive and carries the additional risks associated with regional or general anesthesia.

While musculoskeletal injuries may be associated with physical or mechanical processes, other types of tissue injury may involve physiological processes. For example, myocardial injury from a compromised cardiac vascular system may result in cell ischemia or even cell death. According to the American Heart Association, coronary heart disease is the single leading cause of death in the United States. The prevalence of heart attack in the U.S. was approximately 8.1 million people in 2005, and, of those, 920,000 were new or recurrent. Heart attack is also known as acute myocardial infarction (MI) and occurs when the blood supply to the heart is interrupted—usually by a plaque detaching from and blocking a cardiac blood vessel. As a result of restricted blood flow, the adjacent cardiac tissue becomes ischemic begins to die. If left untreated, an MI will lead to death.

Acute myocardial infarction may comprise non-ST-elevated myocardial infarction or ST-elevated myocardial infarction. In an ST-elevated myocardial infarction, the ST segment in an electrocardiogram (ECG) is elevated, meaning that the ventricles do not depolarize as rapidly as they would in a healthy heart. If blood flow to the heart is impaired over an extended period of time, an ischemic cascade and cardiac apoptosis may occur, causing heart cells to die and not regenerate. In place of the ischemic tissue, scar tissue forms. The scar tissue may increase the likelihood of cardiac arrhythmia, and may result in the formation of ventricular aneurysms.

To treat an MI, reperfusion therapy may be performed. Reperfusion therapies include thrombolytic therapy, percutaneous coronary intervention (PCI), and/or bypass surgery. While reperfusion therapy restores blood flow to the ischemic tissue, it does not lessen the risk of arrhythmia resulting from the growth of scar tissue. Because of the heightened risk of arrhythmia, the patient may be placed on anti-arrhythmia agents and/or require a pacemaker.

As such, additional treatments for treating tissue damage are desirable. Kits for treating tissue damage are also desirable.

SUMMARY

Platelet rich plasma (PRP) compositions for treating tissue damage are provided. The compositions may generally comprise a platelet rich plasma that includes a specific concentration of platelets, red blood cells, and white blood cells. In some examples, the compositions may be characterized relative to a baseline concentration of the platelets, red blood cells, and/or white blood cells of the whole blood from which the compositions are directly or indirectly derived. The PRP composition disclosed herein may be useful in treating connective tissue and/or cardiac tissue. For example, it is believed that the PRP compositions described herein may repair tissue damage by slowing or halting apoptosis, and that the anti-apoptotic effects of the PRP compositions may be measured based on a decrease in caspases in the blood, such as caspase-3.

In some examples, the PRP composition comprises platelet cells at a concentration at least 1.1 times the concentration of platelets in whole blood. The platelet concentration in the PRP composition may be between about 1.1 and about 2 times baseline, about 2 and about 4 times baseline, about 4 and about 6 times baseline, about 6 and about 8 times baseline, or higher. The platelet concentration in the PRP composition may be between about 500,000 and about 1,500,000 platelets per microliter.

The PRP composition may further comprise white blood cells (WBCs) at a higher concentration than white blood cells in whole blood. The WBC concentration may be between about 1.1 and about 2 times baseline, about 2 and about 4 times baseline, about 4 and about 6 times baseline, about 6 and about 8 times baseline, or higher. In some variations, the WBC concentration is about 15,000 to about 50,000 WBC per microliter.

In some variations, the PRP composition may comprise specific concentrations of various types of white blood cells. The concentrations of lymphocytes and monocytes may be between about 1.1 and about 2 times baseline, about 2 and about 4 times baseline, about 4 and about 6 times baseline, about 6 and about 8 times baseline, or higher. The concentrations of eosinophils in the PRP composition may be about 1.5 times baseline. In some variations, the lymphocyte concentration is between about 5,000 and about 20,000 per microliter and the monocyte concentration is between about 1,000 and about 5,000 per microliter. The eosinophil may be between about 200 and about 1,000 per microliter.

In certain variations, the PRP composition may contain a specific concentration of neutrophils. The neutrophil concentration may vary between less than the baseline concentration of neutrophils to eight times the baseline concentration of neutrophils. In some variations, the neutrophil concentration may be between 0 and about 0.1 times baseline, about 0.1 and about 0.5 times baseline, about 0.5 and 1.0 times baseline, about 1.0 and about 2 times baseline, about 2 and about 4 times baseline, about 4 and about 6 times baseline, about 6 and about 8 times baseline, or higher. The neutrophil concentration may additionally or alternatively be specified relative to the concentration of the lymphocytes and/or the monocytes. In preferred embodiments, the neutrophil concentration is less than the concentration in whole blood. In a more preferred embodiment, the neutrophil concentration is 0.1 to 0.9 the concentration found in whole blood, yet more preferably less than 0.1 the concentration found in whole blood. In a most preferred embodiment the neutrophils are eliminated or non-detectable in the PRP composition.

In some embodiments, the PRP compositions may comprise a lower concentration of red blood cells (RBCs) and/or hemoglobin than the concentration in whole blood. The RBC concentration may be between about 0.01 and about 0.1 times baseline, about 0.1 and about 0.25 times baseline, about 0.25 and about 0.5 times baseline, or about 0.5 and about 0.9 times baseline. The hemoglobin concentration may be 5 g/dl or less.

The PRP compositions are typically generated from whole blood or portions of whole blood using a variety of techniques comprising, for example, centrifugation, gravity filtration, and/or direct cell sorting. Once generated the PRP compositions may undergo one or more processes to confirm the concentrations and/or activation of the various components.

In preferred embodiments, any of the PRP compositions described above are prepared from a patient who has not been previously treated with a thrombolytic agent, such as heparin, tPA, PLAVIX®, or aspirin. Preferably, the patient has not received a thrombolytic agent for at least 2 hours, preferably 1 day, more preferably 2 weeks, and yet more preferably 1 month prior to withdrawing the blood for extraction of the PRP. In particular, if a patient is a candidate for reperfusion therapy, the blood to be used for extraction of PRP is drawn from the patient before administering the reperfusion therapy.

Embodiments of the invention are directed to methods of identifying drug candidates for treating a disease or condition based upon a response to a PRP composition, such as a PRP composition described above. In preferred embodiments, a PRP composition as described above is administered as a treatment to an individual suffering from a disease or condition. Alternatively, a model for the disease could be used such as an animal or cell culture system. The PRP composition is administered to the model animal or included in the cell culture media. In other embodiments, simulations are carried out using a computer. The efficacy of the treatment is monitored in the individual or animal model or in the cell culture or the computer simulation. Individuals responsive to the treatment are selected and a sample is obtained from the responsive individual. In the case of a human patient or animal model, this sample might be a bodily fluid sample such as blood or saliva or a tissue sample. In a cell culture, the responsive cells are selected. In a computer model, positive simulations are identified.

Analysis is performed on the biological sample obtained from the patient, animal or cell cultures. Typically such analysis would be by an immunoassay to determine the presence of specific antibodies or antigens or a genetic analysis. The genetic analysis may indicate genes that are upregulated or downregulated. In the case of a computer simulation, parameters are identified indicative of a positive response.

The results obtained as above are compared to results obtained from a non-disease population or a subpopulation having the disease but not responsive to treatment to determine targets present in the responsive population. Based upon the identified targets, drugs candidates, such as proteins or small molecules, for treating the disease condition are identified and further tested.

In preferred embodiments, the disease or condition is ischemia, cancer, a disease of the immune system, a connective tissue injury, a skin disease, or a disease of the nervous system. The ischemia may be a brain ischemia or cardiac ischemia. The cancer may be brain cancer, thyroid cancer, pancreatic cancer, liver cancer, breast cancer, or prostate cancer. The connective tissue injury may be a tendinosis, such as tennis elbow, rotator cuff injury, a knee injury, a spinal injury or plantar fasciitis. The nervous system disease may be Parkinsons' disease.

In preferred embodiments, the PRP composition is depleted in neutrophils, preferably at a level of 0 to 0.9 of the concentration of whole blood.

In preferred embodiments, the analysis involves generation of a genetic profile. For example a DNA array may be used to determine defective genes or may be used to determine patterns of gene expression. In some preferred embodiments, the analysis involves measuring levels of proteins, lipids, antibodies, antigens, enzymes or small molecules.

Embodiments of the invention are directed to a method of disease diagnosis for a patient by one or more of the following steps:
- obtaining a blood sample from the patient;
- obtaining PRP from the blood sample;
- obtaining an analysis from the PRP; and
- comparing the analysis of the PRP from the patient with an analysis obtained from PRP of a population having the disease; and
- determining that analysis of the PRP of the patient matches the analysis of the PRP of the disease population, thereby diagnosing the disease. In preferred embodiments, the analysis is an immunoassay or genetic profile.

Embodiments of the invention are directed to a device having platelet rich plasma composition as described above alone or in combination with a fixation device such as a stent, suture, screw or implantable device. Preferably, the device is a chamber. More preferably, conditions in the chamber include one or more of the following: low oxygen tension, high oxygen tension, low pH, high pH, low pressure, high pressure, low UV, high UV, low temperature and high temperature.

BRIEF DESCRIPTION OF THE DRAWINGS

FIG. 1 is a table of an exemplary PRP composition used in murine models.

DETAILED DESCRIPTION

Overview

Figure 2:
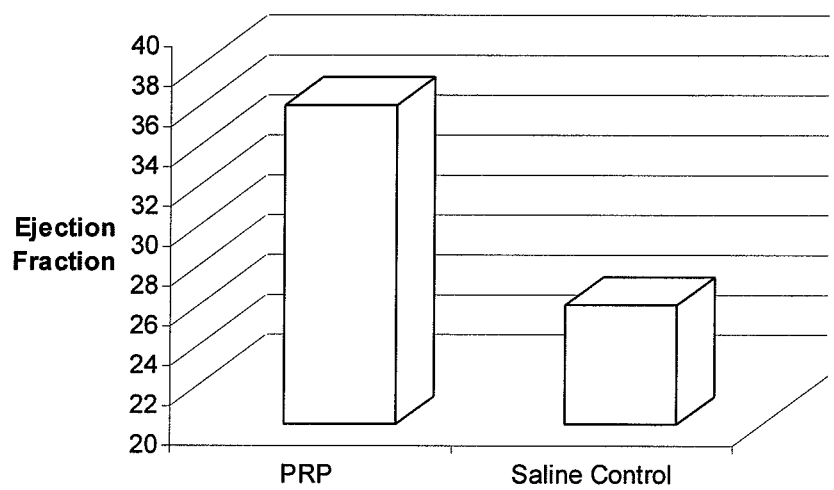
FIG. 2 is a graph comparing the cardiac ejection fraction of subjects treated with the composition to a control group.

Biological compositions that can be used to treat various medical conditions are provided. The biological compositions generally comprise a platelet rich plasma that includes white blood cells and platelets at higher concentrations than those in whole blood. In connective tissue, this PRP composition may be used to treat tissue that has been damaged due to injury, wound, trauma, lesion, and/or tissue degeneration. In cardiac tissue, this PRP composition may be used to treat ischemic tissue following an acute MI to preserve myocardial tissue and promote re-growth. Additionally, the PRP composition may slow or halt apoptosis, reduce infarct size, decrease cardiac arrhythmias, and/or restore cell function.

It has been hypothesized that the PRP composition may promote regrowth by slowing or halting apoptosis. For example, in cardiac tissue, cardiac apoptosis is a process in metazoan cells that contributes to the development of congestive heart failure. Cardiac apoptosis may reduce the number of contractile cardiocytes in the myocardium through programmed cell death. The low, but abnormal, rate of cardiocyte apoptosis may be a significant loss for adult human myocardium, at least in part because adult human cardiocytes have typically lost the ability to replicate. Apoptosis of cardiac non-myocytes may diminish the contractile mass, which may also lead to heart failure. Apoptosis of cardiac non-myocytes may also contribute to maladaptive remodeling and the subsequent transition to decompensated congestive heart failure.

Cardiac apoptosis may be measured by the level of cysteine proteases in the blood. Specifically, caspase-3 is a cysteine-aspartic acid protease that may be used as a marker for cardiac apoptosis. Generally, caspase-3 is an effector caspase that cleaves to protein substrates within the cell resulting in the apoptotic process. A caspase cascade may occur when the caspase-3 is automatically activated between cells. In cardiac tissue, caspase-3 has been shown to significantly rise as early as one day after a myocardial infarction and persist for up to four weeks.

To treat tissue damaged by, for example, apoptosis, injury, wound, trauma, lesion, or degeneration, various methods for delivering the PRP composition into the connective tissue and/or the myocardium are disclosed. In various embodiments, the composition may be delivered to damaged connective tissues, the region of connective tissue directly adjacent to the damaged tissue, and/or healthy tissue. In some embodiments, the PRP composition may be delivered to the ischemic tissues, the region of tissue directly adjacent to the ischemic tissue, and/or healthy tissue. The PRP composition may comprise a platelet gel, or flowable material or liquid, other substances described herein, or any substance suitable for providing the desired level of treatment of the damaged or ischemic tissues.

The PRP composition may be delivered to a patient in an emergency situation or as part of an elective procedure. To treat damaged connective tissue, the PRP composition may be delivered as part of an inpatient or outpatient procedure days, weeks, months, or years after the tissue damage occurred. Examples of connective tissue damage that may be treated using PRP include, but are not limited to, lateral epicondylitis (i.e., tennis elbow), plantar fasciitis, patellar tendonitis (i.e., Jumper's Knee), Achilles tendonitis, rotator cuff tendonitis, ankle sprains, and ligament tears. The tissue damage may be identified using one or more medical imaging technologies such as, but not limited to, x-ray imaging, magnetic resonance imaging (MRI), and ultrasound imaging. To treat damage to the myocardium, the PRP composition may be delivered in an emergency room and/or by emergency medical service providers when an MI is identified. In other instances, the PRP composition may be delivered after an MI during reperfusion therapy.

The MI may be identified by determining whether enzymes such as cardiac troponin (e.g., troponin-I or T), creatine kinase (CK) including CK-MB, aspartate transminase (AST)/Glutamic Oxaloacetic Transaminase (GOT/SGOT)/aspartate aminotransferase (ASAT), lactate dehydrogenase (LDH), and/or myoglobin (Mb), and/or the like are present in the blood stream. The PRP compositions described herein may be delivered in the absence of the enzymes. Myocardial infarctions may be determined by identifying ST elevation in an ECG (e.g., during rest, a pharmacological stress test, and/or a physiological stress test), by coronary angiogram (e.g., noting acute closure of a vessel supplying myocardium at risk), by a nuclear medicine scan (e.g., technetium-99m or thallium-201), etc.

The PRP compositions used to treat the damaged connective tissue or the myocardium may be generated from whole blood or portions of whole blood using a variety of techniques comprising, for example, centrifugation, gravity filtration, and/or direct cell sorting. Once generated, the PRP compositions may undergo one or more processes to confirm the concentrations and/or activation of the various components.

The compositions, devices, methods, and kits described herein are illustrative of various embodiments, variations, and adaptations. The disclosure is not intended to be limited to only the embodiments described.

Compositions

The PRP compositions generally comprise elevated concentrations of platelets and WBCs relative to whole blood. Typically, the concentration of RBCs and hemoglobin is depressed. In some variations, the concentrations of the platelets and the WBCs are specified to increase the likelihood that the PRP composition will effectively treat damaged tissue and/or ischemic tissue.

The PRP composition generally includes platelets at a platelet concentration that is higher than the baseline concentration of the platelets in whole blood. Baseline concentration means the concentration found in the patient's blood which would be the same as the concentration found in a blood sample from that patient without manipulation of the sample by laboratory technique such as cell sorting, centrifugation or filtration. The platelet concentration may be between about 1.1 and about 2 times the baseline, about 2 and about 3 times the baseline, about 3 and about 4 times the baseline, about 4 and about 5 times the baseline, about 5 and about 6 times the baseline, about 6 and about 7 times the baseline, about 7 and about 8 times the baseline, about 8 and about 9 times the baseline, about 9 and about 10 times the baseline, about 11 and about 12 times the baseline, about 12 and about 13 times the baseline, about 13 and about 14 times the baseline, or higher. In some embodiments, the platelet concentration may be between about 4 and about 6 times the baseline. Typically, a microliter of whole blood comprises at least 140,000 to 150,000 platelets and up to 400,000 to 500,000 platelets. The PRP compositions may comprise about 500,000 to about 7,000,000 platelets per microliter. In some instances, the PRP compositions may comprise about 500,000 to about 700,000, about 700,000 to about 900,000, about 900,000 to about 1,000,000, about 1,000,000 to about 1,250,000, about 1,250,000 to about 1,500,000, about 1,500,000 to about 2,500,000, bout 2,500,000 to about 5,000,000, or about 5,000,000 to about 7,000,000 platelets per microliter.

The WBC concentration is typically elevated in the PRP composition. For example, the WBC concentration may be between about 1.1 and about 2 times the baseline, about 2 and about 4 times the baseline, about 4 and about 6 times the baseline, about 6 and about 8 times the baseline, about 8 and about 10 times the baseline, or higher. The WBC count in a microliter of whole blood is typically at least 4,100 to 4,500 and up to 10,900 to 11,000. The WBC count in a microliter of the PRP composition may be between about 8,000 and about 10,000, about 10,000 and about 15,000, about 15,000 and about 20,000, about 20,000 and about 30,000, about 30,000 and about 50,000, about 50,000 and about 75,000 and about 75,000 and about 100,000.

Among the WBCs in the PRP composition, the concentrations may vary by the cell type but, generally, each may be elevated. In some variations, the PRP composition may comprise specific concentrations of various types of white blood cells. The relative concentrations of one cell type to another cell type in a PRP composition may be the same or different than the relative concentration of the cell types in whole blood. For example, the concentrations of lymphocytes and/or monocytes may be between about 1.1 and about 2 times baseline, about 2 and about 4 times baseline, about 4 and about 6 times baseline, about 6 and about 8 times baseline, or higher. In some variations, the concentrations of the lymphocytes and/or the monocytes may be less than the baseline concentration. The concentrations of eosinophils in the PRP composition may be less than baseline, about 1.5 times baseline, about 2 times baseline, about 3 times baseline, about 5 times baseline, or higher.

In whole blood, the lymphocyte count is typically between 1,300 and 4,000 cells per microliter, but in other examples, the lymphocyte concentration may be between about 5,000 and about 20,000 per microliter. In some instances, the lymphocyte concentration may be less than 5,000 per microliter or greater than 20,000 per microliter. The monocyte count in a microliter of whole blood is typically between 200 and 800. In the PRP composition, the monocyte concentration may be less than about 1,000 per microliter, between about 1,000 and about 5,000 per microliter, or greater than about 5,000 per microliter. The eosinophil concentration may be between about 200 and about 1,000 per microliter elevated from about 40 to 400 in whole blood. In some variations, the eosinophil concentration may be less than about 200 per microliter or greater than about 1,000 per microliter.

In certain variations, the PRP composition may contain a specific concentration of neutrophils. The neutrophil concentration may vary between less than the baseline concentration of neutrophils to eight times than the baseline concentration of neutrophils. In some variations, the neutrophil concentration may be between about 0.01 and about 0.1 times baseline, about 0.1 and about 0.5 times baseline, about 0.5 and 1.0 times baseline, about 1.0 and about 2 times baseline, about 2 and about 4 times baseline, about 4 and about 6 times baseline, about 6 and about 8 times baseline, or higher. The neutrophil concentration may additionally or alternatively be specified relative to the concentration of the lymphocytes and/or the monocytes. One microliter of whole blood typically comprises 2,000 to 7,500 neutrophils. In some variations, the PRP composition may comprise neutrophils at a concentration of less than about 1,000 per microliter, about 1,000 to about 5,000 per microliter, about 5,000 to about 20,000 per microliter, about 20,000 to about 40,000 per microliter, or about 40,000 to about 60,000 per microliter. In preferred embodiments, neutrophils are eliminated or substantially eliminated. means to deplete blood products, such as PRP, of neutrophils is known as discussed in U.S. Pat. No. 7,462,268, which is incorporated herein by reference.

Typically, whole blood drawn from a male patient may have an RBC count of at least 4,300,000 to 4,500,000 and up to 5,900,000 to 6,200,000 per microliter while whole blood from a female patient may have an RBC count of at least 3,500,000 to 3,800,000 and up to 5,500,000 to 5,800,000 per microliter. These RBC counts generally correspond to hemoglobin levels of at least 132 g/L to 135 g/L and up to 162 g/L to 175 g/L for men and at least 115 g/L to 120 g/L and up to 152 g/L to 160 g/L for women.

In some embodiments, the PRP compositions may comprise a lower concentration of red blood cells (RBCs) and/or hemoglobin than the concentration in whole blood. The RBC concentration may be between about 0.01 and about 0.1 times baseline, about 0.1 and about 0.25 times baseline, about 0.25 and about 0.5 times baseline, or about 0.5 and about 0.9 times baseline. The hemoglobin concentration may be depressed and in some variations may be about 1 g/dl or less, between about 1 g/dl and about 5 g/dl, about 5 g/dl and about 10 g/dl, about 10 g/dl and about 15 g/dl, or about 15 g/dl and about 20 g/dl.

Methods of Making

The PRP composition may comprise a PRP derived from a human or animal source of whole blood. The PRP may be prepared from an autologous source, an allogenic source, a single source, or a pooled source of platelets and/or plasma. To derive the PRP, whole blood may be collected, for example, using a blood collection syringe. The amount of blood collected may depend on a number of factors, including, for example, the amount of PRP desired, the health of the patient, the severity or location of the connective tissue damage and/or the MI, the availability of prepared PRP, or any suitable combination of factors. Any suitable amount of blood may be collected. For example, about 20 cc to about 150 cc of blood may be drawn. More specifically, about 27 cc to about 110 cc or about 27 cc to about 55 cc of blood may be withdrawn. In some embodiments, the blood may be collected from a patient who may be presently suffering, or who has previously suffered from, connective tissue damage and/or an MI. PRP made from a patient's own blood may significantly reduce the risk of adverse reactions or infection.

In an exemplary embodiment, about 55 cc of blood may be withdrawn into a 60 cc syringe (or another suitable syringe) that contains about 5 cc of an anticoagulant, such as a citrate dextrose solution. The syringe may be attached to an apheresis needle, and primed with the anticoagulant. Blood (about 27 cc to about 55 cc) may be drawn from the patient using standard aseptic practice. In some embodiments, a local anesthetic such as anbesol, benzocaine, lidocaine, procaine, bupivicaine, or any appropriate anesthetic known in the art may be used to anesthetize the insertion area.

The PRP may be prepared in any suitable way. For example, the PRP may be prepared from whole blood using a centrifuge. The whole blood may or may not be cooled after being collected. Isolation of platelets from whole blood depends upon the density difference between platelets and red blood cells. The platelets and white blood cells are concentrated in the layer (i.e., the "buffy coat") between the platelet depleted plasma (top layer) and red blood cells (bottom layer). For example, a bottom buoy and a top buoy may be used to trap the platelet-rich layer between the upper and lower phase. This platelet-rich layer may then be withdrawn using a syringe or pipette. Generally, at least 60% or at least 80% of the available platelets within the blood sample can be captured. These platelets may be resuspended in a volume that may be about 3% to about 20% or about 5% to about 10% of the sample volume.

In some examples, the blood may then be centrifuged using a gravitational platelet system, such as the Cell Factor Technologies GPS System® centrifuge. The blood-filled syringe containing between about 20 cc to about 150 cc of blood (e.g., about 55 cc of blood) and about 5 cc citrate dextrose may be slowly transferred to a disposable separation tube which may be loaded into a port on the GPS centrifuge. The sample may be capped and placed into the centrifuge. The centrifuge may be counterbalanced with about 60 cc sterile saline, placed into the opposite side of the centrifuge. Alternatively, if two samples are prepared, two GPS disposable tubes may be filled with equal amounts of blood and citrate dextrose. The samples may then be spun to separate platelets from blood and plasma. The samples may be spun at about 2000 rpm to about 5000 rpm for about 5 minutes to about 30 minutes. For example, centrifugation may be performed at 3200 rpm for extraction from a side of the separation tube and then isolated platelets may be suspended in about 3 cc to about 5 cc of plasma by agitation. The PRP may then be extracted from a side port using, for example, a 10 cc syringe. If about 55 cc of blood may be collected from a patient, about 5 cc of PRP may be obtained.

As the PRP composition comprises activated platelets, active agents within the platelets are released. These agents include, but are not limited to, cytokines (e.g., IL-1B, IL-6, TNF-α), chemokines (e.g., ENA-78 (CXCL5), IL-8 (CXCL8), MCP-3 (CCL7), MIP-1A (CCL3), NAP-2 (CXCL7), PF4 (CXCL4), RANTES (CCL5)), inflammatory mediators (e.g., PGE2), and growth factors (e.g., Angiopoitin-1, bFGF, EGF, FGF, HGF, IGF-I, IGF-II, PDAF, PDEGF, PDGF AA and BB, TGF-.beta. 1, 2, and 3, and VEGF).

The PRP composition may be delivered as a liquid, a solid, a semi-solid (e.g., a gel,), an inhalable powder, or some combination thereof. When the PRP is delivered as a liquid, it may comprise a solution, an emulsion, a suspension, etc. A PRP semi-solid or gel may be prepared by adding a clotting agent (e.g., thrombin) to the PRP. The gel may be more viscous than a solution and therefore may better preserve its position once it is delivered to target tissue.

In some instances, it may be desirable to deliver the PRP composition as a liquid and have it gel or harden in situ. For example, the PRP compositions may include, for example, collagen, cyanoacrylate, adhesives that cure upon injection into tissue, liquids that solidify or gel after injection into tissue, suture material, agar, gelatin, light-activated dental composite, other dental composites, silk-elastin polymers, Matrigel® gelatinous protein mixture (BD Biosciences), hydrogels and/or other suitable biopolymers. Alternatively, the above mentioned agents need not form part of the PRP mixture. For example, the above mentioned agents may be delivered to the target tissue before or after the PRP has been delivered to the target tissue to cause the PRP to gel. In some embodiments, the PRP composition may harden or gel in response to one or more environmental or chemical factors such as temperature, pH, proteins, etc.

The PRP may be buffered using an alkaline buffering agent to a physiological pH. The buffering agent may be a biocompatible buffer such as HEPES, TRIS, monobasic phosphate, monobasic bicarbonate, or any suitable combination thereof that may be capable of adjusting the PRP to physiological pH between about 6.5 and about 8.0. In certain embodiments, the physiological pH may be from about 7.3 to about 7.5, and may be about 7.4. For example, the buffering agent may be an 8.4% sodium bicarbonate solution. In these embodiments, for each cc of PRP isolated from whole blood, 0.05 cc of 8.4% sodium bicarbonate may be added. In some embodiments, the syringe may be gently shaken to mix the PRP and bicarbonate.

As noted above, the PRP composition may comprise one or more additional agents, diluents, solvents, or other ingredients. Examples of the additional agents include, but are not limited to, thrombin, epinephrine, collagen, calcium salts, pH adjusting agents, materials to promote degranulation or preserve platelets, additional growth factors or growth factor inhibitors, NSAIDS, steroids, anti-infective agents, and mixtures and combinations of the foregoing.

Furthermore, the PRP compositions may comprise a contrast agent for detection by an imaging technique such as X-rays, magnetic resonance imaging (MRI), or ultrasound. Examples of such contrast agents include, but are not limited to, X-ray contrast (e.g., IsoVue), MRI contrast (e.g., gadolinium), and ultrasound contrast.

Methods of Testing

In some variations, the PRP composition may be analyzed and/or modified prior to delivery to the patient. The PRP composition may be modified based on, for example, the condition to be treated, an initial complete blood count, a genetic profile of the patient, and other suitable factors.

In some embodiments, a patient's genetic profile is determined. The PRP composition of healthy individuals having the same or similar genetic profile is determined. A PRP composition is prepared in which components are matched to the PRP of the healthy individual having the same genetic profile. The modified PRP composition is administered to the patient to treat the disease or condition.

In some embodiments, the PRP composition of a patient, successfully recovering from a disease or condition may be used as a model to prepare a PRP composition to administer to a patient diagnosed with the same disease or condition. In other words, the PRP composition is first enriched in components which are effective in treating the disease based upon recovered or recovering individuals. The modified PRP composition is then administered to the patient suffering from the disease.

The PRP, or a portion of the PRP, may be placed into an automated blood analyzer that performs a compete blood count (CBC). As part of the CBC, the automated blood analyzers typically return a count of the number of platelets, WBCs, and RBCs present in the sample. The WBC count may further include counts of lymphocytes, monocytes, basophils, neutrophils, and/or eosinophils. Examples of blood analyzers that may be used include, but are not limited to, Beckman Coulter LH series, Sysmex XE-2100, Siemens ADVIA 120 & 2120, and the Abbott Cell-Dyn series.

It is believed that the effectiveness of treatments using PRP may be at least partially dependent on the genetic profile of the patient. The whole blood of a patient may be tested before and/or after generating the PRP composition to determine if the PRP composition is likely to affect the ability of the tissue to regenerate. Once the PRP has been determined to be useful, it may be delivered to the patient.

In certain variations, one or more genetic markers of a patient's DNA, mRNA, proteins, or the like may be evaluated prior to, during, and/or after delivery of the PRP composition. The patient's DNA, or other biomarkers, is typically captured via a sample such as blood, saliva, or other suitable body fluid or body tissue. The sample may be tested for genetic markers that are correlatable to the effectiveness of treatments using the PRP composition. In some instances, the identified genetic markers may be detectable using a genetic tool such as a gene chip or other genetic expression technology. In some instances, the genes that may be tested for include, but are not limited to, collagen type I (COL1A1), collagen type III (COL3A1), cartilage oligomeric matrix protein (COMP), matrix metalloproteinase-3 (MMP-3), and matrix metalloproteinase-13 (MMP-13). Such genetic tools can be used to measure changes in expression levels, or to detect single nucleotide polymorphisms (SNPs) which may be associated with a disease condition. Many gene chips are commercially available including the Affymetrix Gene Chip®, the Applied Microarrays CodeLink® arrays, and the Eppendorf Dual-Chip & Silverquant®.

In some variations, the genetic tool may be analyzed to determine if the patient is likely to respond (favorably or unfavorably) to the PRP composition and/or to subsequent treatments. In certain variations, the PRP composition may be tested at a range of pH values and/or the pH of the PRP may be modified based at least in part on the genetic profile. In some instances, various genetic profiles may be associated with specific concentrations (or ranges of concentrations) as being more or less effective than other concentrations for various components of the PRP composition. The response to the PRP composition may be slowing or halting of cardiac apoptosis, anti-arrhythmia effects, or otherwise decrease risks associated with reperfusion therapy.

If the CBC returned by the automated blood analyzer is not within specified ranges, the PRP composition may be modified using a filtration device and/or cell sorter. The filtration device may use vacuum and/or gravity to remove a portion of the platelet, WBCs, and/or RBCs. In some variations, a cell sorter may receive a CBC input from an automated blood analyzer and/or a gene chip reader. A user may select or confirm one or more modifications to be made to the PRP composition. Of course, the cell sorter may be used with whole blood, portions of whole blood, and/or PRP. The cell sorter may sort the PRP composition based on electric charge, density, size, deformation, fluorescence, or the like. Examples of cell sorters include the BD FACSAria® cell sorter, the Cytopeia InFlux® cell sorter, those manufactured by Beckman Coulter, the Cytonome Gigasort® cell sorter, and the like.

Use of Platelet Rich Plasma Compositions in Drug Discovery

Embodiments of the invention are directed to the use of platelet rich plasma compositions as described herein in drug discovery. A PRP composition is administered in a model system, preferably a mammalian model, such as a disease model or in the course of a human study or in a non-mammalian system such as a plant. The effects of the administered PRP composition on gene expression is monitored. For example, in one embodiment, the effect of a PRP composition in a cell culture system is studied by molecular analysis of the cells. DNA, RNA, microRNA, and/or epigenetic markers are evaluated to determine efficacy of drugs for a specific disorder. In some preferred embodiments, the mechanism by which platelet rich plasma prevents apoptosis in ischemic tissue or cells is studied to discover an existing or new protein that acts in a rate limiting step or critical path. This protein is then purified and used as a small molecule drug in the treatment of a disease. Dosage of drugs is also evaluated.

In a preferred embodiment, a PRP composition is used in a disease model (in-vitro, animal, human, computer) to evaluate gene expression. Preferably, the disease model is a cell or tissue culture or an animal model or a human study. The PRP composition is used as a test treatment in the disease model compared to no treatment or other known treatments. DNA microarray, RNA, microRNA, epigenetics or other molecular analysis techniques are used to determine changes in gene expression due to the PRP treatment in the model. Cellular gene expression is evaluated and analyzed for patterns. Identified molecules are purified. Drugs are generated for treatment of the specific disorder and tested for efficacy. Specifically, enzymes, proteins or molecules that may be used to treat a specific disorder or condition are identified.

In some embodiments, drug screening is specific for a patient or subpopulation of patients having a disease or condition. In some embodiments, a platelet rich plasma composition is administered to a patient suffering from a disease or condition and the effectiveness of the PRP composition is monitored in the patient. If the treatment is effective, a sample is taken from the patient, typically a bodily fluid such as blood or saliva or a tissue sample. The sample is analyzed for markers associated with recovery. The sample is used to determine the genetic profile of the patient using a DNA array (gene chip) or specific markers. This profile is compared to patients not responsive to the treatment. These may be diseased individual that did not respond to treatment with the PRP composition or healthy individuals. Based upon the difference in genetic profile, specific genes are identified as drug targets for the patient population responsive to the PRP composition. Other markers may be antigens, antibodies or small molecules. Drugs may be selected that mimic the effects of the PRP. Such drugs are candidates for disease treatment.

It should be clear that any and or all types of human, plant and animal disorders can or could be evaluated for potential drug discovery using the methodology outlined above. Also, as time passes new means of evaluating a cell, tissue or organism's genetic expression will be developed. These new techniques could be incorporated into the evaluation and analysis of how platelet rich plasma may be used for drug discovery.

Methods of Use

The PRP composition may be delivered at any suitable dose. In some embodiments, the dose may be between about 1 cc and about 3 cc, between about 3 cc and about 5 cc, between about 5 cc and about 10 cc, between about 10 cc and about 20 cc, or more. The dose may be delivered according to a medical procedure (e.g., at specific points in a procedure) and/or according to a schedule. For example, prior to an elective cardioversion, the PRP composition may be delivered about 24 hours, about 12 hours, about 6 hours, about 2 hours, and/or about 1 hour before the procedure begins.

In some examples, the PRP composition may be delivered to damaged connective tissue in or around affected joints. The PRP composition may be delivered to an individual in need thereof by injection using a syringe or catheter. The PRP composition may also be delivered via a dermal patch, a spray device or in combination with an ointment, bone graft, or drug. It may further be used as a coating on suture, stents, screws, plates, or some other implantable medical device. Finally, it may be used in conjunction with a bioresorbable drug or device.

In a preferred embodiment, the PRP composition is incorporated into suture material. The PRP composition may be woven into the suture material. Alternatively, the suture material could be incubated with PRP prior to use. Incubation times may be from a few seconds up to any convenient time which may be the duration of a medical procedure. The PRP may be incubated with the suture material from a few seconds to hours before use, such as less than 1 minute, 5-10 minutes, 10 minutes to an hour, 1-3 hours, 4-12 hours, 13-24 hours, 1-3 days, or 3-31 days.

The PRP-coated suture material may be conveniently stored in an appropriate chamber. In some embodiments, the PRP-coated suture material may be stored frozen and/or under reduced oxygen concentration or increased oxygen concentration. In some embodiments, the PRP alone or in combination with a fixation device such as suture, a screw, a stent, implantable or other device may be incubated or stored under variable conditions such as low and/or high oxygen tension, low and/or high pH, low and/or high pressure, low and/or high UV or other light conditions, low and/or high temperature. That is, conditions of oxygen tension, pH, pressure, UV or other light or temperature in the chamber vary from physiological and/or ambient conditions.

One specific example is a PRP conditioning chamber that has an oxygen supply that varies with time. The oxygen tension is set at or above 20%, preferably 20-25% oxygen tension, for 2-10 minutes, preferably about five minutes and then slowly or abruptly changed to less than 20% oxygen tension, preferably 2-10% oxygen tension, most preferably about 5% oxygen tension for 2-10 minutes, preferably about five minutes. This relative hypoxic challenge may alter in a positive manner the value of the platelet rich plasma for tissue repair. These oxygen values may vary from 0-100% based on the conditions desired for a specific effect on PRP.

Storage times may vary from such as less than 1 minute, 5-10 minutes, 10 minutes to an hour, 1-3 hours, 4-12 hours, 13-24 hours, 1-3 days, 3-31 days, or 1-12 months or 1-5 years The PRP composition alone or in combination with the fixation device may then be used clinically as appropriate. Suture and/or other devices may also be manufactured together with platelet rich plasma, incorporating the platelet rich plasma composition into the device.

A simple example is incubation of suture with platelet rich plasma for 10-30 minutes, preferably about 15 minutes in a chamber with 20-30% oxygen, preferably about 22% oxygen. The suture may then be used to repair an Achilles tendon or heart valve.

In alternate embodiments, a platelet rich plasma composition is incorporated into the device such as a suture, stents, screws, plates, or some other implantable medical device, during the manufacture of the device. The device in which platelet rich plasma is already incorporated is then used for tissue repair.

In another embodiment, a platelet rich plasma composition is prepared and combined with a stent in an appropriate low oxygen chamber for 1-30 minutes, preferably about 10 minutes. The chamber is then exposed to ultraviolet light for a brief period of time, such as 1-60 seconds, 1-5 minutes, or 5-15 minutes. The stent is then removed from the chamber and implanted into a patient. It is expected that this chamber will improve the biologic activity of the platelet rich plasma and or device.

The site of delivery of the PRP composition is typically at or near the site of tissue damage. The site of tissue damage is determined by well-established methods including imaging studies and patient feedback or a combination thereof. The preferred imaging study used may be determined based on the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques. The patient may also assist in locating the site of tissue injury or damage by pointing out areas of particular pain and/or discomfort.

In some examples, a PRP composition may be used to treat a patient diagnosed with an acute myocardial infarction. Treatment with the PRP composition may occur in the field or in the emergency room setting. Criteria for PRP composition treatment may include positive cardiac markers, ST-elevations, or new wall motion abnormalities identified on echocardiogram, for example. The decision to treat with a PRP composition, and the treatment location(s), may depend upon one or more characteristics of the myocardial infarction. For example, a myocardial infarction may be characterized as a ST-elevation myocardial infarction (STEMI) or non-ST-elevation myocardial infarction (NSTEMI), a Q-wave or non-Q-wave myocardial infarction, and whether they are subendocardial or transmural. Myocardial infarctions may also be characterized anatomically by cardiac wall region and/or the suspected blockage site in the cardiac vasculature. Myocardial infarctions may also be characterized as anterior, lateral, inferior, posterior, septal, or right-ventricular in location, and may involve disease or blockage of the left-anterior descending, left circumflex, left main, posterior-descending and right coronary arteries, for example.

In other examples, timing of the PRP preparation and application may be based upon other treatments that are indicated in a patient with a myocardial infarction. In some instances, a PRP composition may be prepared and delivered before, during, and/or after reperfusion therapy is performed to treat an acute myocardial infarction or a previous myocardial infarction. Reperfusion therapies may include thrombolytic therapy (such as heparin, TPA and or other pharmacologic agents), angioplasty, stenting (including bare metal stents and drug-eluting stents) or coronary artery bypass graft (CABG) surgery. In some instances, reperfusion therapy may be associated with an increased risk of an arrhythmia, including sudden death. Also, it is believed that the etiology of reperfusion arrhythmias or reperfusion arrhythmia risk may be different from the arrhythmia etiologies associated with the myocardial infarction itself. For example, some reperfusion arrhythmias may be caused by triggered activity and/or re-entry. A PRP composition may be prepared before or at the start of a reperfusion procedure, but not used unless an arrhythmia occurs during the procedure. In other reperfusion procedures, the patient may be prophylactically pre-treated with a PRP composition before reperfusion occurs, e.g., before guidewire passage across an occlusion, stent positioning, stent expansion, or reestablishment of coronary flow through a bypass segment.

Results obtained by preparation of PRP from a patient exposed to a thrombolytic agent is significantly different from results obtained if the patient has not been exposed to a thrombolytic agent systemically. Thrombolytic agents include heparin, TPA, plavix, and aspirin.

PRP was prepared prior to heparinization in a porcine model and then after heparinization. There were clear and significant differences as shown in the Table below. Prior to being given heparin systemically, PRP was prepared in a standard fashion and the platelet concentration was found to be 5.12 times baseline. After exposure to heparin using the exact same preparation methods, the platelet concentration was found to be 0.71 times baseline. (See Table below) This change in platelet concentration may result in profound changes in the efficacy of the PRP as a regenerative treatment. Thus, there are clear differences in the PRP composition before and after exposure to heparin.

TABLE

PRP Preparation

| | Whole Blood Platelet Count | PRP Platelet Count | Ratio |
|---|---|---|---|
| Before Heparin | 116 | 594 | 5.12x baseline |
| After Heparin | 685 | 489 | 0.71x baseline |

In some procedures, a PRP composition may be used as a non-specific MI treatment. Thus, the specific type and/or location of the infarction may or may not be identified prior to delivery of the PRP composition to the patient. For example, it may be enough to simply determine that the patient has suffered from, or is currently suffering from, an acute MI. Thus, an ECG is not always required in order to deliver the PRP. Of course, use of an ECG may be beneficial in certain circumstances. For example, the amount of PRP composition prepared and used may vary, based upon whether the MI is accompanied with an elevated ST segment. In some variations, whole blood is withdrawn prior to recording an ECG to begin preparation of the PRP composition. The ECG may then be used to determine an appropriate delivery mechanism simultaneously with the preparation of the PRP composition.

In some variations, the PRP composition is injected into a heart after the location, type, and severity of the MI (or some fraction thereof) has been identified. In certain instances, it may be helpful to identify one or more discrete locations within the heart to deliver the PRP composition in order to increase the likelihood that the treatment will be effective.

The location of the MI may be determined or approximated using various techniques. For example, in some variations, diagnostic procedures such as an electrophysiology study or an electrical mapping study of the heart may be used. In other variations, one or more imaging technologies such as MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques may be used. Other technologies and approaches that may be used include visual inspection during open chest surgical procedures, localized blood flow determinations, local electrical and structural activity, nuclear cardiology, echocardiography, echocardiographic stress test, coronary angiography, magnetic resonance imaging (MRI), computerized tomography (CT) scans, and ventriculography.

PRP compositions that are formulated as gels or other viscous fluids may be difficult to deliver via a needle or syringe. Thus, in variations where the use of a needle or syringe is desirable, it may be desirable to add a gelling and/or hardening agent to the PRP composition in situ. One or more needles or catheters may be configured to deliver the PRP composition and/or the agent simultaneously, or substantially simultaneously, to the cardiac tissue. For example, if a needle is used to deliver the PRP composition, the needle may comprise a plurality of lumens through which the PRP composition and the agent separately travel. Alternatively or additionally, separate needles may be used to deliver the components to the tissue at the same time or one after the other.

The PRP composition may be delivered minimally invasively and/or surgically. For example, the PRP composition may be delivered to the heart using a catheter inserted into the patient via the femoral vein or artery, the internal jugular vein or artery, or any other suitable vein or artery. The PRP composition may be delivered along with one or more medical devices, instruments, or agents to treat the MI and/or other cardiac conditions.

To deliver a PRP composition to the ischemic tissue, a physician may use one of a variety of access techniques. These include surgical (e.g., sternotomy, thoracotomy, minithoracotomy, sub-xiphoidal) approaches, endoscopic approaches (e.g., intercostal and transxiphoidal) and percutaneous (e.g., transvascular, endocardial, and pericardial) approaches. Once access has been obtained, the composition may be delivered via epicardial, endocardial, or transvascular approaches. The composition may be delivered to the cardiac wall tissue or cardiac vessels in one or more locations. This includes intra-myocardial, sub-endocardial, and/or sub-epicardial administration.

Upon gaining access to the ischemic tissues of the heart, the delivery device may be inserted through any appropriate vessel. The distal end of the delivery device may be then placed against the surface of the myocardium and one or more needles may be advanced into tissue. Following delivery of one or more components of the PRP composition, the needles, if any, may be retracted. The delivery device may then be repositioned for additional delivery of one or more components of the composition or may be removed from the patient. Incisions may then be closed using standard techniques.

In practice, the beating heart may be stabilized during the delivery of the PRP composition. For example, in some variations, the beating heart may be slowed or stopped by delivery of one or more drugs and/or by electrical stimulation of the heart. For example, a heart may be stabilized using pharmacologic asystole. Alternatively or additionally, a heart may be stabilized using pacing or other algorithms that render the heart fairly static. These procedures may initiate various cardiac states such as reversible initiation of asystole, fibrillation, or a prolonged refractory state. In still other embodiments, mechanical stabilization of the cardiac tissue may be achieved using any of a variety of mechanical stabilizing systems. In some examples, a combination of stabilizing procedures may be used.

The PRP composition may be delivered during a specific portion of the cardiac cycle, and in these variations, the use of one or more stimulation electrodes to act as a pacemaker during the delivery may be desirable. For example, the beat-to-beat period may be artificially lengthened so as to deliver the PRP composition during a specific phase of the cardiac cycle. In these variations, the delivery device may include one or more stimulation and/or sensing electrodes. For example, sensing electrodes may be used to sense contractions of the heart, thereby allowing the delivery of composition to be timed with cardiac contractions. It may be desirable to deliver one or more components of the PRP composition between contractions of the heart.

In some examples, one or more cardiac sensors may be used during the treatment procedures. The sensors may be any suitable sensor system (e.g., an electrical sensor, a chemical sensor, a pressure sensor, an intravascular imaging sensor, or a biosensor) capable of detecting one or more signals indicative of a cardiac contraction or heartbeat. A cardiac sensor may be used to monitor the electrical activity of the heart by picking up and amplifying electrical signals from the heart and displaying a visual output and/or providing an audio output. For example, the output may be displayed on a display interface. The physician may use this output to inject the needles and/or composition into the tissue at a specific point in the cardiac cycle. The cardiac sensor may be coupled to a cardiac stimulator to manipulate or control the cardiac rhythm.

In some variations, a nerve stimulator may be used to electrically manipulate cardiac rhythm by stimulating the vagus nerve. Vagal stimulation may produce asystole (slowing or stopping of the heart). Once the vagal stimulation is stopped, the heart may return to a normal rhythm. Alternatively, the heart may be paced. Vagal stimulation, alone or in combination with electrical pacing, may be used selectively and intermittently to allow a physician to perform delivery of one or more components of the composition into a temporarily stopped heart.

Typically, vagal stimulation may slow or even prevent the heart from contracting. Following initial slowing or stopping of the heart, one or more components of the PRP composition may be delivered to the heart. Following a brief interval of nerve stimulation while the delivery may be performed, nerve stimulation may be ceased and the heart may be allowed to contract. A cardiac stimulator or pacemaker may be used to cause the heart to contract or the heart may be free to beat on its own. In some variations, one or more electrodes may be used for pacing the heart as desired. A processor may control both cardiac and nerve stimulation. For example, a processor may cease nerve stimulation and automatically begin cardiac stimulation.

The delivery system may deliver the components of the PRP composition in a prescribed ratio (e.g., a ratio of the WBCs and the platelets). The prescribed ratio may be calculated beforehand or determined on an ad hoc basis once delivery begins. To deliver the components in the prescribed ratio, the delivery device may include one or more gears having a corresponding gear ratio, one or more lumens having a proportional lumen size, or any other suitable mechanism. Some delivery devices may include one or more mixing chambers. The multiple components may be delivered using separate delivery devices or may be delivered one after the other using the same delivery device.

The delivery devices may be advanced through a vessel adjacent to the ischemic tissue to be treated. The PRP composition may be injected directly into the ischemic tissue using a needle and/or a needle-tip catheter. The PRP composition may alternatively or additionally be infused into the vessel.

When the PRP compositions are delivered using one or more catheters, any suitable catheter may be used. For example, the catheters may include one or more lumens and staggered or flush tips. The catheters may include needles or other devices (e.g., imaging devices) located at the distal end, and plungers or any other control located at the proximal end. The catheters and/or other delivery devices may have differently sized lumens to deliver multiple components of the PRP composition in the prescribed ratio. When catheters are used, a physician may navigate to the heart using one of the routes known for accessing the heart through the vasculature, including but not limited to navigation to a heart chamber for epicardial, endocardial, and/or transvascular delivery of the PRP composition.

Endocardial delivery of the PRP composition may comprise accessing a treatment site, for example, in the left ventricle of a heart, using a delivery device advanced percutaneously in an anterograde approach through the superior vena cava or inferior vena cava into the right ventricle. The delivery device may be passed through the interatrial septum into the left atrium and then into the left ventricle to reach treatment site. Alternatively, the device may be advanced using a transseptal procedure, e.g., through the intraventricular septum into the left ventricle. In another embodiment, the PRP composition may be injected directly into the interventricular septum from the right ventricle. An alternative endocardial delivery method may comprise accessing the treatment site using a delivery device advanced percutaneously in a retrograde approach through the aorta into the left atrium and then into the left ventricle.

Transvascular delivery of compositions may comprise passing the delivery device through the coronary sinus into the cardiac venous system via the cardiac veins and, if needed, leaving the veins by tracking through myocardial tissue. An alternative transvascular delivery method comprises accessing a treatment site through the aorta into a coronary artery to reach treatment site.

The devices for injecting or delivering the PRP compositions (catheter or otherwise) may include cooled parts or other temperature control mechanisms to keep the PRP composition at a desired temperature. Various embodiments of delivery devices may include a cooled chamber, and/or an agitator mechanism in a PRP chamber or injection chamber to prevent settling or clumping of the PRP components. For example, in some variations, the catheter or other delivery device has a cooled lumen or lumens for keeping the PRP composition cool during delivery. The delivery devices may additionally or alternatively include a mixing chamber for mixing the PRP composition prior to delivery. The PRP composition may also be stored in an agitating/vibrating chamber, or the physician may agitate the PRP composition once inside the delivery device by tilting or otherwise manipulating the device.

A practitioner may make multiple deliveries into various locations using a single device, make multiple deliveries into various locations using multiple devices, make a single delivery to a single location using a single device, or make a single delivery to a single location using multiple devices. The deliver devices may include at least one reusable needle or catheter. Some embodiments may include delivery devices having an automated dosing system (e.g., a syringe advancing system). The automated dosing system may allow each dose to be pre-determined and dialed in (may be variable or fixed). In some embodiments, an iontophoresis device may be used to deliver the PRP composition into the ischemic tissue.

The PRP composition may alternatively or additionally be coated on one or more devices such as, for example, sutures, stents, screws, and/or plates. Anti-arrhythmia devices, such as pacemaker leads and automatic defibrillators may also be coated, sprayed, or dipped into the PRP composition prior to, simultaneously with, or subsequently to implantation.

It may be desirable to deliver the PRP composition to the ischemic tissues while avoiding coincidental delivery to other cardiac tissues or other locations adjacent to the heart. For example, the PRP composition may gel or harden upon delivery to prevent migration. In some variations, a balloon catheter may be placed in the coronary sinus and inflated during delivery until the PRP composition has solidified or at least partially immobilized. Other variations may include a pressure control system on the delivery device to prevent pressure-driven migration of the PRP composition. Backbleed may also be prevented by keeping the needle in place for several seconds (e.g., about 5 to about 30 seconds, or about 5 to about 120 seconds) following an injection.

Sensors may be used to direct the delivery device to a desired location and/or to deliver the PRP composition. For example, real-time recording of electrical activity (e.g., an ECG), pH, oxygenation, metabolites such as lactic acid, $CO_2$, or the like may be used. The sensors may be one or more electrical sensors, fiber optic sensors, chemical sensors, imaging sensors, structural sensors, and/or proximity sensors that measure conductance. The sensors may be incorporated into the delivery device or be separate from the delivery device. In some embodiments, the sensors may sense and/or monitor such things as needle insertion depth, blood gas, blood pressure or flow, hemocrit, light, temperature, vibration, voltage, electric current, power, and/or impedance. The sensors may include one or more imaging systems and may be coupled to any appropriate output device, for example, a LCD or CRT monitor which receives and displays information.

The total volume of the PRP composition delivered to the patient may be based on the size of the heart, the amount of the affected ischemic tissue, and/or the desired outcome of the procedure. For example, the total volume of composition injected may be less than 15000 µL.

The number of delivery sites in the heart may be based on the type and location of the infarct(s), the desired location of the PRP composition, and the distance separating the desired locations. The number of delivery sites may range from about 1 to about 25 sites. The distance separating delivery sites may vary based on the desired volume of platelet gel to be delivered per delivery site, the desired total volume to be delivered, and/or the condition of the ischemic tissue. At the delivery site, the PRP composition may be injected, infused, or otherwise disposed at or adjacent to the ischemic tissue. The PRP composition may also be infused into the vasculature (i.e., vessels) upstream of the target site, so that it will flow towards the affected ischemic tissue.

The location of the delivery sites may vary based on the size and shape of the ischemic tissue, and the desired extent of the treatment of the tissue. For example, the PRP composition may be delivered into the ischemic tissue, and/or into the tissue that bordering the ischemic tissue. Similarly, the composition may be delivered to any combination of the regions of ischemic tissue and other cardiac tissue.

The timing of PRP delivery relative to an acute MI may be based on the severity of the infarction, the extent of the ischemic tissue, the condition of the patient, and the progression of any concurrent MI or arrhythmia treatments. The PRP composition may be delivered at any suitable time. For example, it may be delivered immediately after the onset of an MI, within one hour of an MI, one to eight hours following an MI, or three to four days after an MI after clinical stabilization of the patient when it is safer for the patient to undergo a separate procedure. The timing may be based upon the level of caspase-3 in the blood. In some variations, the composition is delivered about one week, about 1 to about 3 weeks, about 1 to about 6 months, or even up to or more than about 1 year after the MI. Other times for injecting compositions into the ischemic tissue are also contemplated, including prior to any potential MI, and immediately upon finding an area of ischemic tissue. Of course, compositions may be injected into the ischemic tissue years after an MI.

After reperfusion, the devices and methods may be used in conjunction with current anti-arrhythmia therapies and/or concurrently with other medical procedures that are generally known to increase the likelihood of an arrhythmia. For example, and as discussed generally with respect to the methods and devices, various cardiac procedures may require slowing (bradycardia) and/or stopping (asystole) the heart for a period of time.

As mentioned previously, a PRP composition may additionally or alternatively be used in other cardiac procedures. These cardiac procedures may include anti-arrhythmia procedures, procedures to correct congenital heart defects, or other pathologies. Examples of other cardiac procedures include, but are not limited to, angioplasty, coronary artery bypass, Minimally Invasive Direct Coronary Artery Bypass (MIDCAB), off-pump coronary artery bypass, Totally Endoscopic Coronary Artery Bypass (TECAB), aortic valve repair, aortic valve replacement, mitral valve repair, mitral valve replacement, Ross procedure, Bentall procedure, pulmonary thromboendarterectomy, transmyocardial revascularization (TMR), valve-sparing aortic root replacement, cardiomyoplasty, Dor procedure, heart transplantation, septal myectomy, ventricular reduction, pericardiocentesis, pericardiectomy, atrial septostomy, Blalock-Taussig shunt procedure, Fontan procedure, Norwood procedure, Rastelli procedure, Maze procedure (Cox maze and minimaze), and/or pacemaker insertion. The PRP composition may used to prevent an arrhythmia associated with reperfusion of the cardiac tissue during any of the above procedures. As is known, reperfusion may cause a spontaneous arrhythmia to occur after cardiac surgery.

The PRP composition may be used alone and or in combination with other therapies including, but not limited to, stems cells (embryonic or adult), cord blood, drugs, genetically engineered molecules, or other bioactive substances.

Kits

Kits may include any device, component, or combination of devices and/or components described herein. For example, the kits may include one or more preparation devices, one or more delivery devices, one or more collection devices, and/or instructions for use. The one or more preparation devices may be for preparing PRP and may comprise a centrifuge, for example. The one or more delivery devices may be configured to deliver a PRP composition comprising the PRP to damaged connective tissue or to a region of the heart to treat an MI. The one or more collection devices may comprise one or more syringes, apheresis needles, or other devices for collecting blood from a patient. The patient may be presently suffering or have suffered an MI and/or connective tissue damage. The components of the kit may be packaged in sterile containers. The kits may comprise one or more single-use components. Instructions may be in written or pictograph form, or may be on recorded media including audio tape, audio CD, video tape, DVD, CD-ROM, or the like.

In addition to the foregoing uses for the compositions, methods and systems described herein, it will be apparent to those skilled in the art that other injured tissues, in addition to injured cardiac tissue and connective tissue, would benefit from the delivery of structural support materials to treat the injuries. Non-limiting examples of such tissues include the stomach, to reduce food intake and increase satiety; the abdominal wall, to prevent and treat hernias; and the bladder to prevent or treat incontinence. Such tissues may additionally include vascular tissues.

EXAMPLES

Example 1

Treatment of Myocardial Infarction with PRP in a Mouse Model

PRP was prepared using a centrifuge unit such as the Biomet GPS system, the Depuy Symphony machine, the Medtronic Magellan machine, those made by Harvest (Plymouth, Mass.), Genesis Enterprises, Sorin Medical, and Regen Lab. Approximately 55 cc of human whole blood was drawn using a standard sterile syringe, combined with 5 cc of a citrate dextrose solution for anticoagulation, and then spun down to isolate the platelets according to the manufacturer's protocol. These platelets were then resuspended in approximately 3 cc of plasma. The various concentrations are shown in the table in FIG. 1.

The human-derived PRP composition or saline control was injected intramuscularly into the myocardium of a murine model after permanent left anterior descending artery ligation. This ligation resulted in a myocardial infarction or heart attack. Ejection fraction measured at seven days by MRI. As shown in FIG. 2, the ejection fraction seven days after the ligation, the ejection fraction of the saline control was 26% while the ejection fraction of the group treated with PRP was 36%.

Example 2

Preparation of PRP Before Administration of Anticoagulant Agent

Whole blood is drawn immediately upon presentation to the emergency room in a patient with a suspected heart attack. Blood may be sent for lab work but also enough extra blood is drawn to prepare platelet rich plasma (PRP) before the administration of heparin, TPA, plavix, aspirin and or other pharmacologic or interventions agents. The PRP is saved for delivery after initiation of reperfusion therapy and/or delivered prior to such intervention.

The PRP can be prepared using a variety of techniques including, but not limited to, centrifuges, gravity filtration devices, cell sorting or others. It can be combined with stem cells, genetic engineering or mechanical devices such as permanent or bioabsorbable pacemaker or stent. The PRP can be made and then stored in a frozen or lyophilized state. In a preferred form it would be buffered to physiologic pH but it may also be valuable to instill PRP at either acidic or basic pH for specific clinical indications such as ablation of an abnormal conduction pathway. In yet another embodiment, the PRP could be prepared in a form that is depleted of neutrophils or other fractions of white blood cells either partially or completely.

Example 3

Use of PRP in Drug Discovery for Ischemia-Related Conditions

Platelet rich plasma is used in an ischemia reperfusion trial (such as a heart attack) in an in-vitro, animal or human model. Analysis of expression of tissues or cells is done at different time points. Computer analysis of microarray output is done to seek out specific upregulation or downregulation of markers of apoptosis, cell regulation or any new or existing signaling pathways. Genes upregulated or downregulated in response to PRP are identified. Drugs affecting these identified genes are tested for their effects on ischemic conditions. On the basis of the genetic expression, drugs useful for the treatment of ischemia or reperfusion tissue issue injury such as what can occur with a heart attack, a stroke or a traumatic injury are identified.

Example 4

Use of PRP in Drug Discovery for Cancer Treatments

A treatment employing a PRP composition is used in a cancer trial in an in-vitro, animal or human model. For example, PRP could be injected into or around a tumor. The effects of the treatment on gene expression is determined using microarrays. Computer analysis of microarray output is done to seek out specific upregulation or downregulation of markers of apoptosis, cell regulation or any new or existing signaling pathways. Based on genetic expression in successfully treated individuals, genes are identified which are upregulated or downregulated in response to effective treatment. Drugs affecting the identified genes are used for the treatment of cancers of any or all types including but not limited to brain cancer, lung cancer, breast cancer, colon cancer or other neoplastic disorders.

Example 5

Use of PRP in Drug Discovery for Connective Tissue Injury

A PRP composition is used as in examples 3 and 4. Another disease state or disorder is identified such as a connective tissue injury including but not limited to tendon, ligament, cartilage, spinal disc, muscle, bone, or others. Specific protocols are developed to evaluate the genetic expression of cells or tissue with and without the addition of platelet rich plasma or its derivatives in a variety of doses or formulations. This expression is then analyzed to seek out novel targets for drug development for such disorders.

While methods, devices, and kits have been described in some detail here by way of illustration and example, such illustration and example may be for purposes of clarity of understanding only. It will be readily apparent to those of ordinary skill in the art in light of the teachings herein that certain changes and modifications may be made thereto without departing from the spirit and scope of the appended claims.

What is claimed is:

1. A composition comprising:
   platelets in a concentration of about 500,000/µl to about 7,000,000/µl,
   monocytes in a concentration of about 400/µl to about 3200/µl, and
   neutrophils in a concentration of less than about 5000/µl,
   lymphocytes in a concentration of about 2600/µl to about 16000/µl,
   wherein the composition does not include an exogenous activator.

2. The composition of claim 1, wherein the concentration of platelets is between about 600,000 platelets/µl and about 5,000,000 platelets/µl.

3. The composition of claim 1, wherein the concentration of platelets is between about 700,000 platelets/µl and about 2,500,000 platelets/µl.

4. The composition of claim 1, wherein the concentration of platelets is between about 900,000 platelets/µl and about 1,500,000 platelets/µl.

5. The composition of claim 1, wherein the concentration of neutrophils is less than about 1000/µl.

6. The composition of claim 1, wherein the hemoglobin concentration is about 1.0 g/dL to about 5 g/dL.

7. The composition of claim 1, wherein the hemoglobin concentration is 1 g/dL or less.

8. A method of preparing the composition of claim 1 comprising:
   mixing components from a starting material to obtain the composition, wherein the starting material comprises at least in part whole blood, said composition comprising:
   platelets in a concentration of about 500,000/µl to about 7,000,000/µl,
   monocytes in a concentration of about 400/µl to about 3200/µl,
   lymphocytes in a concentration of about 2600/µl to about 16000/µl and
   neutrophils in a concentration of less than about 5000/µl.

9. The method of claim 8, wherein the platelet concentration is between 2-8 times the platelet concentration in the starting material.

10. The method of claim 8, wherein the neutrophil concentration is less than about 1000/µl.

11. A method of preparing the composition of claim 1 comprising:
    mixing components from a source of whole blood to obtain the composition, said composition comprising:
    platelets in a concentration of about 500,000/µl to about 7,000,000/µl,
    monocytes in a concentration of about 400/µl to about 3200/µl,
    lymphocytes in a concentration of about 2600/µl to about 16000/µl and
    neutrophils in a concentration of less than about 5000/µl.

12. The method of claim 11, wherein the platelet concentration is between 2-8 times the platelet concentration in the whole blood.

13. The method of claim 12, wherein the platelet concentration is between 4-6 times the platelet concentration in the whole blood.

14. The method of claim 11, wherein the hemoglobin concentration is less than about 3.5 grams per deciliter.

15. The method of claim 11, wherein the neutrophil concentration is less than about 1000/µl.

16. The method of claim 11, wherein the composition is prepared from the whole blood via centrifugation, gravity filtration, or direct cell sorting.

17. The method of claim 11, wherein the composition further comprises:
    white blood cells derived from the whole blood at a concentration of at least a white blood cell concentration in the whole blood, wherein the white blood cells comprise:
    monocytes at a concentration of at least about two times a monocyte concentration in the whole blood; and
    lymphocytes at a concentration of at least about two times a lymphocyte concentration in the whole blood.

* * * * *

UNITED STATES PATENT AND TRADEMARK OFFICE
CERTIFICATE OF CORRECTION

PATENT NO. : 8,444,969 B2
APPLICATION NO. : 13/333082
DATED : May 21, 2013
INVENTOR(S) : Mishra It is certified that error appears in the above-identified patent and that said Letters Patent is hereby corrected as shown below:

On the Title Page

In column 1 (page 2 item [56] Other Publications) at line 38, Under Other Publications, Change "applicaton" to --application--.

In column 1 (page 2 item [56] Other Publications) at line 58, Under Other Publications, Change "cotler," to --coller,--.

In column 2 (page 2 item [56] Other Publications) at line 11, Under Other Publications, Change "opthalmologic" to --ophthalmologic--.

In column 2 (page 2 item [56] Other Publications) at line 31, Under Other Publications, Change "lschemia,"" to --Ischemia,"--.

In the Specification

In column 6 at line 51, Change "transminase" to --transaminase--.

In column 7 at line 41, Change "bout" to --about--.

In column 8 at line 41, Change "means" to --Means--.

In column 9 at line 25, Change "bupivicaine," to --bupivacaine,--.

In column 10 at line 5, Change "Angiopoitin-1," to --Angiopoietin-1,--.

In column 12 at line 65, Change "and or" to --and/or--.

In column 14 at line 23, Change "and or" to --and/or--.

In column 14 at line 66, Change "and or" to --and/or--.

In column 18 at lines 30-31, Change "transeptal" to --transseptal--.

In column 19 at line 38, Change "hemocrit," to --hematocrit,--.

In column 20 at line 45, Change "may" to --may be--.

In column 20 at line 50, Change "and or" to --and/or--.

In column 21 at line 54, Change "and or" to --and/or--.

Signed and Sealed this
Twenty-second Day of October, 2013

Teresa Stanek Rea
*Deputy Director of the United States Patent and Trademark Office*